US00PP30141P2

(12) United States Plant Patent
Meilland

(10) Patent No.: US PP30,141 P2
(45) Date of Patent: Jan. 29, 2019

(54) BEDDING ROSE PLANT NAMED 'MEITRALIGH'

(50) Latin Name: *Rosa hybrida*
Varietal Denomination: Meitraligh

(71) Applicant: The Conard-Pyle Company, West Grove, PA (US)

(72) Inventor: Alain Antoine Meilland, Antibes (FR)

(73) Assignee: The Conard-Pyle Company, West Grove, PA (US)

( * ) Notice: Subject to any disclaimer, the term of this patent is extended or adjusted under 35 U.S.C. 154(b) by 0 days.

(21) Appl. No.: 15/731,823

(22) Filed: Aug. 9, 2017

(51) Int. Cl.
*A01H 5/02* (2018.01)

(52) U.S. Cl.
USPC ..... Plt./108
CPC ..... *A01H 5/02* (2013.01)

(58) Field of Classification Search
USPC ..... Plt./108, 115
CPC ..... A01H 5/0222
See application file for complete search history.

(56) References Cited

PUBLICATIONS https://issuu.com/starrosesandplants/docs/2018 catalog; Apr. 27, 2017; 1 page.*

* cited by examiner

*Primary Examiner* — Kent L Bell
(74) *Attorney, Agent, or Firm* — Buchanan Ingersoll & Rooney PC

(57) ABSTRACT

A new and distinct variety of Bedding rose plant, herein referred to by its cultivar name, 'Meitraligh', is provided which forms in abundance on a nearly continuous basis attractive, flat cup-shaped, red colored flower. Dense, semi-glossy foliage is formed and the plant is very floriferous. The tolerance to pest and disease is excellent, particularly with respect to black spot. The new variety is well suited for providing attractive ornamentation in the landscape.

1 Drawing Sheet

Figures 1, 2, 3, 4, 5, 6, 7, 8, 9, 10, 11, 12, 13, 14:
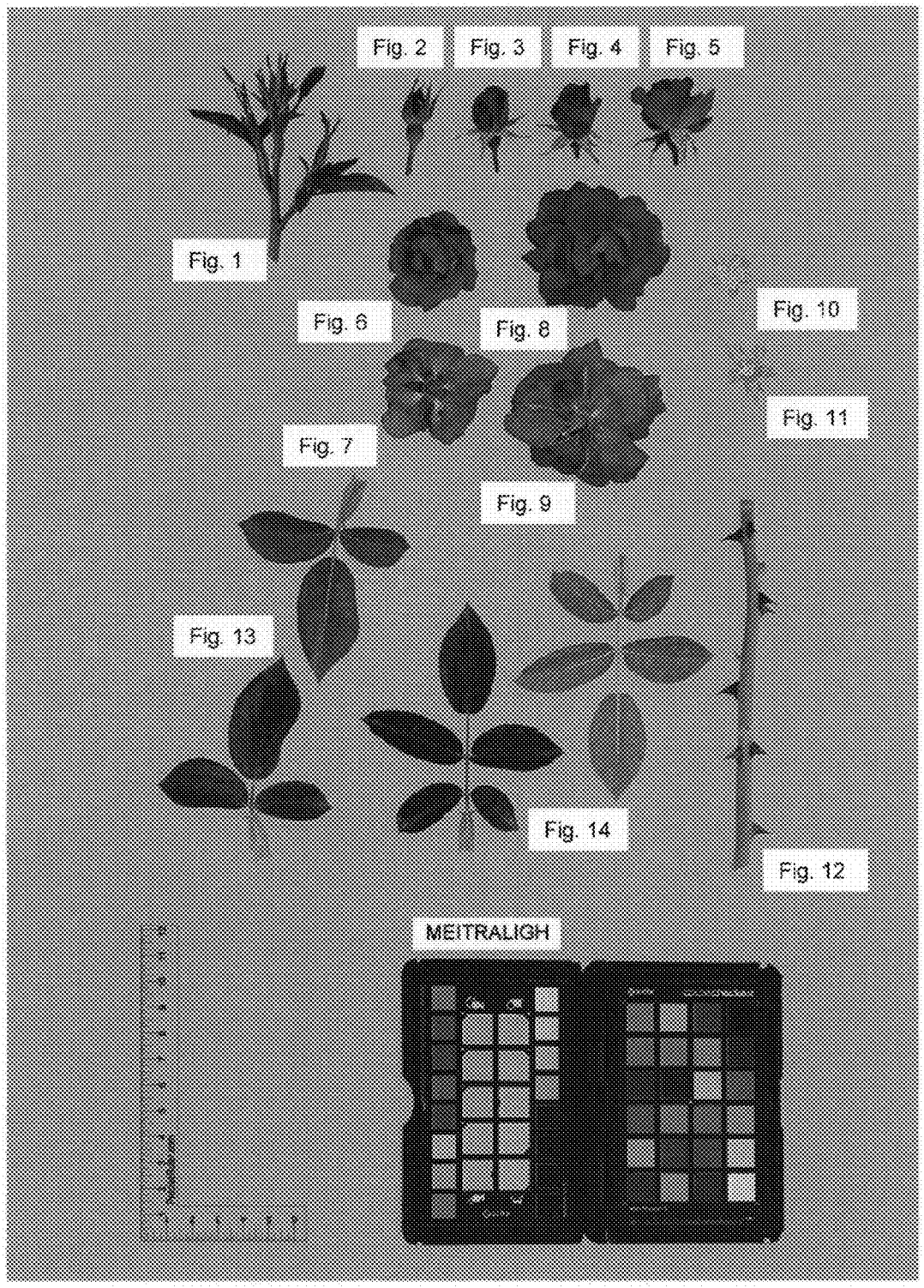

Botanical/commercial classification:
Latin name—*Rosa hybrida.*
Common name—Bedding Rose Plant.
Varietal denomination—'Meitraligh'.

SUMMARY OF THE INVENTION

The new variety of *Rosa hybrida* Bedding rose plant of the present invention was created by artificial pollination wherein two parents were crossed which previously had been studied in the hope that they would contribute the desired characteristics. The female parent (i.e., seed parent) of the new variety was the 'Noawel' variety (non-patented in the United States). The male parent (i.e., pollen parent) was the 'Meidanu' variety (non-patented in the United States).

The parentage can be summarized as follows:

'Noawel' x 'Meidanu'.

The seeds resulting from the above pollination were sown and small plants were obtained which were physically and biologically different from each other. Selective study resulted in the identification of a single plant of the new variety.

It was found that the new Bedding rose plant of the present invention possesses the following combination of characteristics:

(a) displays a very floriferous plant,
(b) exhibits a red coloration of the flower which is a beautiful contrast with the dense and semi-glossy foliage,
(c) blooming is early in the season and is very abundant and nearly continuous, (d) shows an excellent resistance to pests and disease, particularly with respect to black spot, and
(e) is well suited for providing attractive ornamentation.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the 'Noawel' variety displays a ground cover habit while the new variety displays a bushy growth habit, and the 'Meidanu' variety has more petals than the new variety.

The new variety has been found to undergo asexual propagation in France by a number of routes, including budding, grafting, and the rooting of cuttings. Asexual propagation by the above-mentioned techniques in France has shown that the characteristics of the new variety are stable and strictly transmissible by such asexual propagation from one generation to another. Accordingly, the new variety undergoes asexual propagation in a true-to-type manner.

The new variety has been named 'Meitraligh'.

BRIEF DESCRIPTION OF THE PHOTOGRAPHS

The accompanying photographs show, as nearly true as it is reasonably possible to make the same in color illustrations of this character, typical specimens of the new variety. The illustrated rose plants of the new variety were approximately two years of age and were observed during September while budded on their own roots and growing outdoors at Le Cannet des Maures, Var, France. Dimensions in centimeters are indicated at the bottom of the photograph. Standard color information is included at the bottom of the photograph.

FIG. 1—illustrates a specimen of a young shoot.

FIG. 2—illustrates a specimen of a floral bud before the opening of the sepals.

FIG. 3—illustrates a specimen of a floral bud at the opening of the sepals.

FIG. 4—illustrates a specimen of a floral bud at the opening to the petals.

FIG. 5—illustrates a specimen of a flower in the course of opening.

FIG. 6—illustrates a specimen of a flower in the course of opening—plan view—obverse.

FIG. 7—illustrates a specimen of a flower in the course of opening—plan view—reverse.

FIG. 8—illustrates a specimen of a fully open flower—plan view—obverse.

FIG. 9—illustrates a specimen of a fully open flower—plan view—reverse.

FIG. 10—illustrates a specimen of a floral receptacle showing arrangement of the stamens and pistils.

FIG. 11—illustrates a specimen of a floral receptacle showing arrangement of the pistils (stamens removed).

FIG. 12—illustrates a specimen of a flowering stem.

FIG. 13—illustrates a specimen of a leaf with 3 leaflets—plan view—upper and under surface.

FIG. 14—illustrates a specimen of a leaf with 5 leaflets—plan view—upper and under surface.

DETAILED BOTANICAL DESCRIPTION

The chart used in the identification of colors is that of The Royal Horticultural Society (R.H.S. Colour Chart, 2001 Edition), London, England. The terminology which precedes reference to the chart has been added to indicate the corresponding color in more common terms. The description is based on the observation of two-year-old specimens of the new variety during September while budded on their own roots and growing outdoors at Le Cannet des Maures, Var, France.

Class: Bedding Rose Plant.

Plant:

*Habit*.—Bushy.

Branches:

*Color*.—Commonly near Yellow Green Group 144A on young stems, and commonly near Yellow Green Group 146A/B on adult wood.

*Thorns*.—Configuration on adult stems: slightly curved downwards on the upper surface and concave on the under surface with an oval shaped base. Long prickles (≥0.8 cm) — quantity: commonly approximately 4 thorns per 10 cm long young stem and commonly approximately 10 thorns per 10 cm long adult stems. Long prickles (≥0.8 cm) — color: commonly near Yellow Green Group 152C on young stems and commonly near Greyed Orange Group 164A on adult stems. Long prickles (≥0.8 cm) — size: commonly near 0.9 cm in length on average on young stems and commonly near 1.2 cm in length on average on adult stems. Small prickles (<0.8 cm): none observed.

Foliage:

*General appearance*.—Very dense with a semi-glossy aspect.

*Leaf*.—Length: approximately 10 cm to 12 cm on average. Width: approximately 7 to 9 cm on average.

*Number of leaflets*.—3, 5, and 7; most often 5.

*Terminal leaflet*.—Length: approximately 5 cm on average. Width: approximately 3.5 cm on average.

*New foliage*.—Upper surface color: commonly near Yellow Green Group 146A. Under surface color: commonly near Yellow Green Group 146B.

*Adult foliage*.—Upper surface color: commonly near Yellow Green Group 146A. Under surface color: commonly near Yellow Green Group 146B.

Leaflets:

*Shape*.—Tip: pointed. Base: obtuse.

*Texture*.—Leathery.

*General appearance*.—Elliptical.

*Edge*.—Slightly denticulate.

*Serration*.—Small and single.

*Petiole rachis*.—Color of upper surface: commonly near Yellow Green Group 146C. Color of under surface: commonly near Yellow Green Group 146D.

*Petioles*.—Upper surface texture: glandular, with few glands. Under surface texture: few prickles. Color of upper surface: commonly near Yellow Green Group 146C. Color of under surface: commonly near Yellow Green Group 146D. Petiole length of terminal leaflet: near 1.2 cm on average.

*Stipules*.—General appearance: adnate, pectinate, and narrow. Length: near 1 cm on average. Width: near 0.5 cm on average. Color of upper surface: commonly near Yellow Green Group 148D. Color of under surface: commonly near Yellow Green Group 146D.

Inflorescence:

*Number of flowers per stem*.—Commonly 1 to 9 blossoms per stem.

*Buds*.—Shape: conical. Size: small. Length: approximately 1.2 cm on average. Width: approximately 1 cm on average. Color as calyx breaks — upper surface: commonly near Red Group 46C amply suffused with near Red Group 46B. Color as calyx breaks — under surface: commonly near Red Group 53B.

*Sepals*.—Length: approximately 2 cm on average. Width: near 0.6 cm on average. Shape: longish and narrow at the top and rounded at the base with no extension. Upper surface texture: tomentous. Upper surface color: commonly near Yellow Green Group 148D. Under surface texture: smooth. Under surface color: commonly near Yellow Green Group 144D.

*Receptacle*.—Color: commonly near Yellow Green Group 144A. Length: approximately 0.9 cm on average. Width: approximately 0.6 cm on average. Surface: smooth. Shape: pitcher shaped.

*Peduncle*.—Length: near 3 to 3.5 cm on average. Width: approximately 0.2 cm on average. Surface: glandular. Color: commonly near Yellow Green Group 144A amply suffused with near Greyed Red Group 178A.

*Flower*.—Average open size: typically near 5 cm to 7 cm. Shape: flat cup shaped. Number of petals: commonly 14 to 16 on average. Petal shape: obtuse at the base and rounded at the top. Petal texture: leathery. Petal length: approximately 3 cm on average. Petal width: approximately 2.9 cm on average. Petal arrangement: imbricated without petaloids. Petal drop: petals drop off cleanly before drying. Fragrance: none. Color when opening — upper surface: commonly near Red Group 46C amply suffused with near Red Group 46B. Color when opening — under surface: commonly near Red Group 53B. Color of the open flower — upper surface: commonly near Red Group 46C amply suffused with near Red Group 46B. Color of the open flower — under surface: commonly near Red Group 53B. Anthers: number is approximately 63 on average, length is approximately 0.1 cm on average, coloration is commonly near Yellow Orange Group 17D, and arrangement is regular around styles. Filaments: length is approximately 0.3 cm on average, and coloration is commonly near Yellow Group 2D. Styles: number is approximately 42 on average, length is approximately 0.1 cm on average, and coloration is commonly near Yellow Group 2D. Stigmas: size is approximately 0.4 cm on average, and coloration is commonly near Yellow Green Group 44D. Hip: none observed.

Development:

*Vegetation*.—Very strong.

*Blooming*.—Early in the season, very abundant and nearly continuous.

*Tolerance to diseases*.—Excellent, particularly against black spot (Diplocarpon rosae).

Plants of the 'Meitraligh' variety have not been observed under all possible environmental conditions to date. Accordingly, it is possible that the phenotypic expression may vary somewhat with changes in light intensity and duration, cultural practices, and other environmental conditions.

I claim:

1. A new and distinct Bedding rose plant characterized by the following combination of characteristics:

(a) displays a very floriferous plant, (b) exhibits a red coloration of the flower which is a beautiful contrast with the dense and semi-glossy foliage, (c) blooming is early in the season and is very abundant and nearly continuous, (d) shows an excellent resistance to pests and disease, particularly with respect to black spot, and (e) is well suited for providing attractive ornamentation; substantially as herein shown and described.

* * * * *

MEITRALIGH